(12) United States Patent
Janssens et al.

(10) Patent No.: US 7,282,508 B2
(45) Date of Patent: Oct. 16, 2007

(54) SUBSTITUTED 4-PHENYL-4-(1H-IMIDAZOL-2-YL)-PIPERIDINE DERIVATIVES AND THEIR USE AS SELECTIVE NON-PEPTIDE DELTA OPIOID AGONISTS

(75) Inventors: Frans Eduard Janssens, Bonheiden (BE); Joseph Elisabeth Leenaerts, Rijkevorsel (BE); Francisco Javier Fernández-Gadea, Toledo (ES); Antonio Gómez-Sánchez, Toledo (ES); Theo Frans Meert, Beerse (BE)

(73) Assignee: Janssen Pharmaceutica N.V. (BE)

( * ) Notice: Subject to any disclaimer, the term of this patent is extended or adjusted under 35 U.S.C. 154(b) by 382 days.

(21) Appl. No.: 10/491,379

(22) PCT Filed: Oct. 10, 2002

(86) PCT No.: PCT/EP02/11372
§ 371 (c)(1),
(2), (4) Date: Mar. 31, 2004

(87) PCT Pub. No.: WO03/033486
PCT Pub. Date: Apr. 24, 2003

(65) Prior Publication Data
US 2004/0260096 A1 Dec. 23, 2004

(30) Foreign Application Priority Data
Oct. 15, 2001 (EP) .................... 01203926

(51) Int. Cl.
A61K 31/445 (2006.01)
C07D 401/00 (2006.01)
(52) U.S. Cl. ..................... 514/326; 546/210
(58) Field of Classification Search ................ 514/256, 514/326; 544/333; 546/210
See application file for complete search history.

(56) References Cited

U.S. PATENT DOCUMENTS 5,354,863 A 10/1994 Dappen et al.
6,444,679 B1 * 9/2002 Liras et al. ................. 514/256

FOREIGN PATENT DOCUMENTS

| EP | 864559 | 2/1998 |
|---|---|---|
| EP | 1038872 A1 | 2/2000 |
| JP | 4275288 | 9/1992 |
| WO | WO 9315062 | 8/1993 |
| WO | WO 9504734 | 2/1995 |
| WO | WO 9531461 | 5/1995 |
| WO | WO 9622276 | 7/1996 |
| WO | WO 9710216 | 3/1997 |
| WO | WO 9828270 | 7/1998 |
| WO | WO 9828275 | 7/1998 |
| WO | WO 9852929 | 11/1998 |
| WO | WO 00/37470 | 6/2000 |
| WO | WO 0146192 | 6/2001 |

OTHER PUBLICATIONS

Liras et al. "preparation of 4-phenyl . . . " CA 133:222737 (2000).*
Hackh's chemical dictrionay, McGraw-Hill Co. pl. 27 (1983).*
Wermuth "The practice of medicinal chemistry" Acd. press, p. 203-213 (1996).*
Jong et al. "The design and synthesis of . . . " Bioorg. Med. Chem. Lett. 14 p. 181-185 (2004).*
Lord J.A.H. et al., Nature 1977, 267, 495-499.
Moulin et al., Pain, 1985, 23, 213-221.
Goodman and Gilman, The Pharmacological Basis of Therapeutics, 9th Edition, McGraw-Hill, 1996, 521-555.
Galligan et al., J. Pharm. Exp. Ther. 1984, 229, 641-648.
Dondio et al., Review: Non-peptide δ-opioid agonists and antagonists, Exp. Opin. Ther. Patents, 1997, 10, 1075-1098.
Stella, V.J. et al., "Prodrugs", Drug Delivery Systems, 1980, pp. 112-176.
Stella, V.J. et al., Drugs, 1985, 29, pp. 455-473.
Malatynska E., et al al., "Human δopioid Receptor: A stable cell line for functional studies of opioids", NeuroReport 6, 613-616, 1995.
Portoghese, P.S., et al., "Naltrindole, a highly selective and potent non-peptide δ opioid receptor antagonist", Eur. J. Pharmacol. 146, 185-186, 1988.
Alt, A. et al., "Stimulation of guanosine-5'O'(3[35S]thio)triphosphate binding by endogenous opioids acting at a cloned Mu receptor", J. Pharmacol. Exp. Ther. 286, 282-288, 1988.
Smart, D., et al., "The effects of recombinant rat μ-opioid receptor activation in CHO cells on phospholipase C, [Ca$^{2+}$]I and adenylyl cyclase", Br. J. Pharmacol. 120, 1165-1171, 1997.
Bradford, M.M., "A rapid and sensitive method for the quantification of microgram quantities of protein utilizing the principle of protein-dye binding", Analytical Biochem, 72: 248-254, 1976.
Lazareno, S., "Measurement of agonist-stimulated [35S]GTPγS binding to cell membranes" Meth. Molec. Biol. 106, 231-243, 1999.

* cited by examiner

Primary Examiner—Celia Chang
(74) Attorney, Agent, or Firm—Woodcock Washburn LLP

(57) ABSTRACT

The present invention relates to novel 4-phenyl-4-[1H-imidazol-2-yl]-piperidine derivatives according to Formula (I)

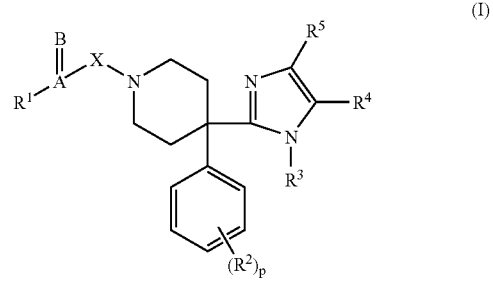

the pharmaceutically acceptable acid or base addition salts thereof, the stereochemically isomeric forms thereof, the tautomeric forms thereof and the N-oxide forms thereof. In particular are claimed compounds according to Formula (I) in which A=B is C=O or $SO_2$, X is a covalent bond, $R^1$ is alkyloxy, alkyloxyalkyl, Ar or $NR^9R^{10}$, wherein $R^9$ and $R^{10}$ each independently are hydrogen or Ar; or A=B and $R^1$ together form a benzoxazolyl radical; p is zero, $R^3$ is benzyl optionally substituted with hydroxy, alkyl or alkyloxycarbonyl and $R^4$ and $R^5$ each are hydrogen. The invention also relates to processes for the preparation of the compounds according to the invention and their use in medicine, in particular as selective non-peptide δ-opioid agonists for use in the treatment of various pain conditions.

3 Claims, No Drawings

SUBSTITUTED 4-PHENYL-4-(1*H*-IMIDAZOL-2-YL)-PIPERIDINE DERIVATIVES AND THEIR USE AS SELECTIVE NON-PEPTIDE DELTA OPIOID AGONISTS

CROSS REFERENCE TO RELATED APPLICATIONS

This application is the national stage of Application No. PCT/EPO02/11372, filed Oct. 10, 2002, which application claims priority from EP 01203926.9 filed Oct. 15, 2001.

The present invention relates to novel 4-phenyl-4-[1H-imidazol-2-yl]-piperidine derivatives, processes for their preparation and their use in medicine, in particular as selective non-peptide d-opioid agonists.

The presence of at least three populations of opioid receptors (commonly known as mu (μ), delta (d) and kappa (κ) receptors) is now well established and documented and all three populations appear to be present in the central and peripheral nervous system of many species, including man (Lord J. A. H. et al., *Nature* 1977, 267, 495).

Modulation of one or more of these opioid receptor subtypes may lead to a variety of effects observed in animal models, giving rise to unique pharmacological profiles for each receptor. For instance, d-agonists seem to exert an analgesic effect (both spinal and supraspinal) in different pain conditions in mice, rats, rodents, primates and even in man (Moulin et al. *Pain*, 1985, 23, 213), increase the release of growth hormone and inhibit dopamine release, while d-antagonists have no analgesic effect and decrease the release of growth hormone. (Goodman and Gilman, *The Pharmacological Basis of Therapeutics*, 9th Edition, McGraw-Hill, 1996, 525).

Some experiments also suggest that d-analgesics may also lack the usual side effects associated with μ- and κ-receptor activation (Galligan et al., *J. Pharm. Exp. Ther.* 1984, 229,641).

Animal models have also demonstrated that d-opioid receptor agonists may exert a direct effect on the gastrointestinal (e.g. antidiarrhoeal effect) and respiratory tract (e.g. stimulatory effect on respiratory activity). Furthermore, it has been shown that d-opioid receptor agonists may play a synergistic role in a variety of pharmacological effects. In fact, they positively modulate the central antinociception and antitussive activity of μ-agonists, resulting in a diminished dose regimen delaying the untoward side-effects associated to these narcotic drugs. Interestingly, the immunostimulatory activity of some d-opioid receptor agonists may be of value in the development of therapeutic strategies for immune deficient disorders in man (Dondio et al. Review: Non-peptide d-opioid agonists and antagonists, *Exp. Opin. Ther. Patents*, 1997, 10, 1075).

In view of their important pharmacological value, there is a need for d-opioid receptor agonists that are selective both in their action as agonists (showing weak or no antagonist action) and for the d-receptor (showing weak or no preference for the μ- or κ-opioid receptor subtype). Furthermore, such d-opioid receptor agonists should not be peptidic in nature as such compounds are unstable for administration by systemic routes.

Currently known non-peptidic delta opioid receptor agonists comprise indolo- and benzofuranomorphinans (U.S. Pat. No. 5,354,863 (1994) by Searle & Co, WO-9531464 (1995) by Astra A B), octahydroisoquinolines (e.g. TAN-67 by Toray Inc., published in JP-4275288 (1992) and WO-9710216 (1997) by Smithkline Beecham SPA), piperazine derivatives (e.g. BW373U86 and SNC 80 by The Welcome Foundation, published in WO-9315062 (1993)), pyrrolooctahydroisoquinolines (WO-9504734 (1995) by Smithkline Beecham SPA), ethylamine derivatives (WO-9622276 (1996) by Nippon Shinyaku Co. Ltd.), triazaspirodecanones (WO 0146192 (2001) by Meiji Seika Kaisha Ltd.) and substituted amino-derivatives (EP-864559 (1998) by Gruenenthal Gmbh).

WO-9828270 (1998) and WO-9828275 (1998) by Astra A B discloses piperidine-derivatives with analgesic activity. Said compounds are not structurally related to the compounds of the present invention.

EP 1 038 872 A1(2000) by Pfizer Products Inc. disclose certain 4-phenyl-4-heteroarylpiperidine derivatives as opioid receptor ligands. Said compounds differ structurally from the ones in the current application—among other—in nature of the piperdinyl nitrogen substitution, which lacks the bivalent π-bond radical substitution.

In WO 00/37470 (2000) by Janssen Pharmaceutica N.V. is generally disclosed a pathway for the synthesis of antihistaminic spiro-compounds using some compounds according to the invention. However, said compounds have not exemplified in the prior art application, nor is there any suggestion that they might have d-opioid receptor agonists properties.

It is the object of the present invention to provide a novel class of highly selective d-opioid receptor agonists, based on a piperidine-moiety It is another object of the present invention to provide d-opioid receptor agonists useful as analgesics having reduced side-effects. It is the further object of the present invention to provide d-opioid receptor agonists active for d-opioid receptor mediated diseases.

SUMMARY OF THE INVENTION

The present invention relates to novel substituted 4-phenyl-4-[1H-imidazol-2-yl]-piperidine derivatives derivatives according to the general Formula (I)

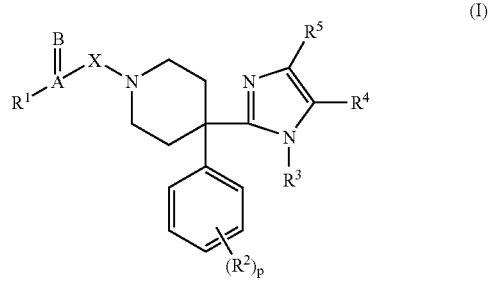

the pharmaceutically acceptable acid or base addition salts thereof, the stereochemically isomeric forms thereof, the tautomeric forms thereof and the N-oxide forms thereof, wherein:
A═B is bivalent π-bond radical;
X is a covalent bond, —CH$_2$— or CH$_2$CH$_2$—;
R$^1$ is hydrogen, alkyloxy, alkylcarbonyloxy, Ar-oxy, Het-oxy, Ar-carbonyloxy, Het-carbonyloxy, Ar-alkyloxy, Het-alkyloxy, alkyl, polyhaloalkyl, alkyloxyalkyl, Ar-alkyl, Het-alkyl, Ar, Het, thio, alkylthio, Ar-thio, Het-thio or $NR^9R^{10}$ wherein $R^9$ and $R^{10}$ each independently are hydrogen, alkyl, Ar, Ar-alkyl, Het, Het-alkyl, Ar-carbonyl, Het-carbonyl or alkyloxycarbonylalkyl; or A═B and $R^1$ together form an optionally substituted semi-aromatic or aromatic carbocyclic or heterocyclic radical $Het^2$ or $Het^3$;

$R^2$ is hydroxy, alkyloxy, alkylcarbonyloxy, phenyloxy, phenylcarbonyloxy, halo, cyano, alkyl, polyhaloalkyl, alkyloxyalkyl, formyl, carboxy, alkylcarbonyl, alkyloxycarbonyl, aminocarbonyl, mono- or dialkylaminocarbonyl, phenyl, nitro, amino, mono- or dialkyl-amino, thio or alkylthio;

$R^3$ is alkyl, Ar, Ar-alkyl, Ar-alkenyl, Ar-carbonyl, Het, Het-alkyl, Het-alkenyl or Het-carbonyl;

$R^4$, $R^5$ each independently is hydrogen, alkyl, carboxy, aminocarbonyl, alkyloxycarbonyl, halo or hydroxyalkyl;

p is an integer equal to zero, 1, 2 or 3;

DETAILED DESCRIPTION OF THE INVENTION

In the framework of this application, alkyl is a straight or branched saturated hydrocarbon radical having from 1 to 6 carbon atoms; or is a cyclic saturated hydrocarbon (cycloalkyl) radical having from 3 to 7 carbon atoms; or is a cyclic saturated hydrocarbon radical having from 3 to 7 carbon atoms attached to a straight or branched saturated hydrocarbon radical having from 1 to 6 carbon atoms; wherein each carbon atom may be optionally substituted with amino, nitro, thio, hydroxy, oxo, cyano, formyl or carboxy. Preferably, alkyl is methyl, ethyl, propyl, isopropyl, butyl, tert-butyl, cyclopropyl, cyclopentyl, cyclohexyl, cyclohexylmethyl and cyclohexylethyl.

In the framework of this application, alkenyl is an alkyl radical as defined above having one or more double bonds. Preferably, alkenyl is ethenyl and propenyl.

In the framework of this application, Ar is a homocycle selected from the group of phenyl and naphthyl, each optionally substituted with one or more substituents, each substituent independently selected from the group of hydroxy, alkyloxy, alkylcarbonyloxy, phenyloxy, phenylcarbonyloxy, halo, cyano, alkyl, polyhaloalkyl, alkyloxyalkyl, formyl, haloformyl, carboxy, alkylcarbonyl, alkyloxycarbonyl, aminocarbonyl, mono- or dialkylaminocarbonyl, phenylalkyl, phenyl, nitro, amino, mono- or dialkyl-amino, thio, alkylthio or $SO_2$—$CH_3$. Preferably, Ar is naphthyl or phenyl, each optionally substituted with hydroxy, methyloxy, ethyloxy, phenyloxy, trihalomethyloxy, halo, methyl, trifluoromethyl, chloroformyl, carboxy, methyloxycarbonyl, ethyloxycarbonyl, diethylaminocarbonyl, phenyl, nitro, methylthio, trifluoromethyloxy or $SO_2$—$C_{1-3}$alkyl.

In the framework of this application, halo is a substituent selected from the group of fluoro, chloro, bromo and iodo and polyhaloalkyl is a straight or branched saturated hydrocarbon radical having from 1 to 6 carbon atoms or a cyclic saturated hydrocarbon radical having from 3 to 7 carbon atoms, wherein one or more carbon atoms is substituted with one or more halo-atoms. Preferably, halo is bromo, fluoro or chloro and preferably, polyhaloalkyl is trifluoromethyl.

In the framework of this application, Het is a heterocyclic radical selected from the group of $Het^1$, $Het^2$ and $Het^3$. $Het^1$ is an aliphatic monocyclic heterocyclic radical selected from the group of pyrrolidinyl, dioxolyl, imidazolidinyl, pyrazolidinyl, piperidinyl, dioxyl, morpholinyl, dithianyl, thiomorpholinyl, piperazinyl and tetrahydrofuryl. $Het^2$ is a semi-aromatic monocyclic heterocyclic radical selected from the group of 2H-pyrrolyl, pyrrolinyl, imidazolinyl and pyrazolinyl. $Het^3$ is an aromatic monocyclic heterocyclic radical selected from the group of pyrrolyl, pyrazolyl, imidazolyl, furyl, thienyl, oxazolyl, isoxazolyl, thiazolyl, isothiazolyl, pyridinyl, pyrimidinyl, pyrazinyl, pyridazinyl or triazinyl; or an aromatic bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocyclic radical may optionally be substituted on a carbon and/or an heteroatom with halo, hydroxy, alkyloxy, alkyl, Ar, Ar-alkyl or pyridinyl.

An interesting group of compounds are those compounds according to Formula (I), the pharmaceutically acceptable acid or base addition salts thereof, the stereochemically isomeric forms thereof, the tautomeric forms thereof and the N-oxide forms thereof, in which A═B is selected from the group of C═O, C═N—$R^6$ wherein $R^1$ is hydrogen or cyano, C═S, S═O, $SO_2$ and C═$CR^7R^8$ wherein $R^7$ and $R^8$ each independently are hydrogen, nitro or alkyl.

Another interesting group of compounds are those compounds according to Formula (I), the pharmaceutically acceptable acid or base addition salts thereof, the stereochemically isomeric forms thereof, the tautomeric forms thereof and the N-oxide forms thereof, in which $R^1$ is selected from the group of alkyloxy, Ar-alkyloxy, alkyl, polyhaloalkyl, alkyloxyalkyl, Ar-alkyl, Het-alkyl, Ar, piperazinyl, pyrrolyl, thiazolyl, pyrrolidinyl and $NR^9R^{10}$ wherein $R^9$ and $R^{10}$ each independently are hydrogen, alkyl, Ar, Ar-alkyl, pyridinyl or alkyloxycarbonylalkyl.

Another interesting group of compounds are those compounds according to Formula (I), the pharmaceutically acceptable acid or base addition salts thereof, the stereochemically isomeric forms thereof, the tautomeric forms thereof and the N-oxide forms thereof, in which A═B and $R^1$ together form a radical selected from the group of $Het^2$ and $Het^3$. More preferably, A═B and $R^1$ together form a radical selected from the group of benzoxazolyl, thiazolyl, benzothiazolyl, benzimidazolyl and pyrimidinyl.

Yet another interesting group of compounds are those compounds according to Formula (I), the pharmaceutically acceptable acid or base addition salts thereof, the stereochemically isomeric forms thereof, the tautomeric forms thereof and the N-oxide forms thereof, in which X is a covalent bond or a —$CH_2$-moiety. Preferably, X is a covalent bond.

Yet another interesting group of compounds are those compounds according to Formula (I), the pharmaceutically acceptable acid or base addition salts thereof, the stereochemically isomeric forms thereof, the tautomeric forms thereof and the N-oxide forms thereof, in which $R^2$ is alkyloxy or halo.

Yet another interesting group of compounds are those compounds according to Formula (I), the pharmaceutically acceptable acid or base addition salts thereof, the stereochemically isomeric forms thereof, the tautomeric forms thereof and the N-oxide forms thereof, in which $R^3$ is selected from the group of phenylalkyl and naphthyl, each independently substituted with at least one substituent selected from the group of halo, alkyloxycarbonyl, hydroxy, alkyloxy and dialkylaminocarbonyl.

When $R^3$ is alkyl, then preferentially, alkyl is cyclohexylmethyl.

Still another interesting group of compounds are those compounds according to Formula (I), the pharmaceutically acceptable acid or base addition salts thereof, the stereochemically isomeric forms thereof, the tautomeric forms thereof and the N-oxide forms thereof, in which A=B is C=O or $SO_2$, $R^1$ is alkyloxy, alkyloxyalkyl, Ar or $NR^9R^{10}$, wherein $R^9$ and $R^{10}$ each independently are hydrogen or Ar; or A=B and $R^1$ together form a benzoxazolyl radical; p is zero, $R^3$ is benzyl optionally substituted with hydroxy, alkyl or alkyloxycarbonyl and $R^4$ and $R^5$ each are hydrogen.

More specifically, the following compounds are the most preferred compounds:

1-ethoxycarbonyl-4-phenyl-4-[1-(phenylmethyl)-1H-imidazol-2-yl]-piperidine;

1-propyloxycarbonyl4-phenyl-4-[1-(phenylmethyl)-1H-imidazol-2-yl]-piperidine;

1-ethoxycarbonyl-4-phenyl-4-[1-[(4-hydroxyphenyl)methyl]-1H-imidazol-2-yl]-piperidine;

1-ethoxycarbonyl-4-phenyl-4-[1-(1-phenylethyl)-1H-imidazol-2-yl]-piperidine;

1-isopropyloxycarbonyl-4-phenyl-4-[1-phenylmethyl)-1H-imidazol-2-yl]-piperidine;

1-ethoxycarbonyl-4-phenyl-4-[1-[[4-(methoxycarbonyl)phenyl]methyl]-1H-imidazol-2-yl]-piperidine;

1-benzoyl-4-phenyl-4-[1-(phenylmethyl)-1H-imidazol-2-yl]-piperidine;

1-(methoxyacetyl)-4-phenyl-4-[1-(1-phenylethyl)-1H-imidazol-2-yl]-piperidine;

4-[[2-(1-benzoyl-4-phenyl-4-piperidinyl)-H-imidazol-1-yl]methyl]-methylbenzoate;

4-[[2-[1-(2-benzoxazolyl)-4-phenyl-4-piperidinyl]-1H-imidazol-1-yl]methyl]-methylbenzoate;

1-benzoyl4-phenyl4-[1-(1-phenylethyl)-1H-imidazol-2-yl]-piperidine;

1-ethoxycarbonyl-4-phenyl-4-[1-[1-[4-(ethoxycarbonyl)phenyl]ethyl]-1H-imidazol-2-yl]-piperidine and N,4-diphenyl-4-[1-(phenylmethyl)-1H-imidazol-2-yl]-1-piperidinesulfonamide.

The pharmaceutically acceptable acid addition salts are defined to comprise the therapeutically active non-toxic acid addition salt forms which the compounds according to Formula (I) are able to form. Said acid addition salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, mandelic acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to Formula (I) as well as the salts thereof, are able to form. Such solvates are, for example, hydrates and alcoholates.

The term "stereochemically isomeric forms" as used herein defines all possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of Formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

We note that the substituted carbon atom in the 4-position in the piperidinyl moiety is an achiral atom; therefore, compounds of Formula (I) may only have at least one stereogenic center in their structure by virtue of a chiral substituent $R^1$, $R^2$, $R^3$, $R^4$ or $R^5$.

The tautomeric forms of the compounds of Formula (I) are meant to comprise those compounds of Formula (I) wherein e.g. an enol group is converted into a keto group (keto-enol tautomerism).

The N-oxide forms of the compounds according to Formula (I) are meant to comprise those compounds of Formula (I) wherein one or several nitrogen atoms are oxidized to the so-called N-oxide, particularly those N-oxides wherein the nitrogen of the piperidine moiety and/or the imidazole moiety is oxidized.

The compounds of Formula (I) as prepared in the processes described below may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a C$_{1-6}$alkyl, phenyl, benzyl or one of the following groups:

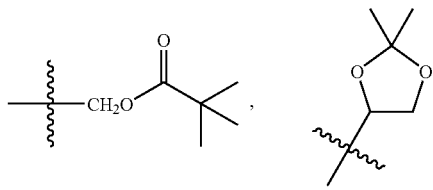

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to the invention have surprisingly been shown to be useful in therapy, especially for the treatment of various pain conditions, such as and in particular centrally mediated pain, peripherally mediated pain, structural or soft tissue injury related pain, progressive disease related pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes and cluster or migraine headeaches.

The compounds according to the invention can also be useful for the treatment of arthritis, psoriasis, asthma, inflammatory bowel disease, respiratory function disorder, functional diarrhea, non-ulcerogenic dyspepsia and incontinence. Such use has also been documented in WO/9852929 (Pfizer Ltd, 1998).

The presence of delta opioid receptors on the human colon has also been demonstrated by both radioligand binding and autoradiographic studies. The greatest density of binding (80-90%) has been located to the neurones of the myenteric plexus situated between the circular and longitudinal smooth muscle layers, with a low density of receptors located on the smooth muscle layers. In functional studies, delta-opioid agonists can inhibit both cholinergic and non-cholinergic excitatory neurotransmission in the human colon. Based on these observations, delta-opioid receptor agonists would be expected to inhibit colonic motility in man. It has also been shown that the peripherally acting selective delta-opioid agonist UK-321130 exhibited potent, dose-related inhibition of colonic motility in pre-clinical models. Therefor, the compounds of the present invention are also claimed for the treatment of irritable bowel syndrome (IBS).

The present invention thus relates to compounds of Formula (I) as defined hereinabove, the pharmaceutically acceptable acid or base addition salts thereof, the stereochemically isomeric forms thereof, the tautomeric forms thereof and the N-oxide forms thereof, for use as a medicine.

In vitro receptor and neurotransmitter signal transduction studies can be used to evaluate the delta, mu and kappa opioid receptor agonist activities, as described further in this application.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration by parenteral injection or infusion. For example, in preparing the compositions, any of the usual pharmaceutical media may be employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredient, and, from 1 to 99.95% by weight, more preferably from 30 to 99.9 weight % of a pharmaceutically acceptable carrier, all percentages being based on the total composition.

The pharmaceutical composition may additionally contain various other ingredients known in the art, for example, a stabilizing agent, buffering agent, emulsifying agent, viscosity-regulating agent, surfactant or preservative.

Further, the present invention also relates to the use of a compound of Formula (I), the pharmaceutically acceptable acid or base addition salts thereof, the stereochemically isomeric forms thereof, the tautomeric forms thereof and the N-oxide forms thereof, as well as any of the aforementioned pharmaceutical compositions thereof for the manufacture of a medicament for the treatment of various pain conditions, such as and in particular centrally mediated pain, peripherally mediated pain, structural or soft tissue injury related pain, progressive disease related pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes, cluster or migraine headeaches, arthritis, psoriasis, asthma, inflammatory bowel disease, respiratory function disorder, functional diarrhea, non-ulcerogenic dyspepsia, incontinence and irritable bowel syndrome (IBS).

Accordingly, in another aspect, the invention provides a method of treating a human suffering from any of the above mentioned conditions, which comprises administering to the human in need of such a treatment a therapeutically effective amount of a compound or pharmaceutical composition according to the invention.

The compounds of the present invention in isotopically labeled form are useful as a diagnostic agent. The present invention therefor also relates to those isotopically labeled compounds, as well as a diagnostic method using the isotopically labeled compounds according to the present invention.

The compounds according to the invention can generally be prepared by a succession of steps, each of which is known to the skilled person. In particular, the compounds according to Formula (I-a) can be prepared by reacting an intermediate of Formula (II) according to reaction scheme (1), a reaction that is performed in a suitable reaction-inert solvent, such as toluene, in the presence of a suitable base, such as triethylamine In reaction scheme (1), all variables are defined as in Formula (I) and $W^1$ together with the moiety it is attached to is equal to $R^1$; examples of $W^1$ are alkyl, Ar or Het. An example of $W^1OC(=O)Cl$ is chloroformiate.

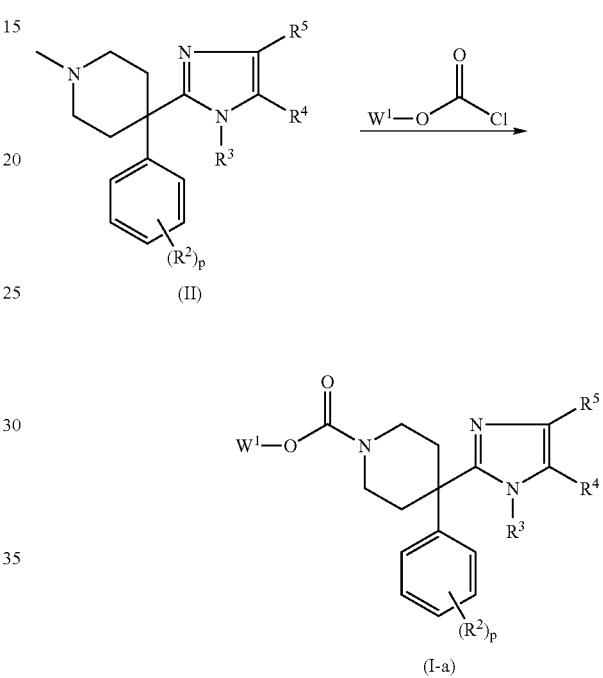

Scheme 1

(II)

(I-a)

The compounds according to Formulas (I-a), (I-b), (I-c), (I-d), (I-e), (I-f), (I-g) and (I-h) can also be prepared by reacting an intermediate of Formula (III) according to any of the reactions shown in reaction scheme (2). In said reactions, all variables are defined as in Formula (I) and $W^1$ together with the moiety it is attached to is equal to $R^1$; examples of $W^1$ are alkyl, Ar or Het.

Reaction (a) is performed in a suitable solvent such as dichloroethane and using $BOC_2O$. The reaction is conveniently carried out for several hours under reflux.

Reaction (b) is performed in a suitable solvent such as THF. The reaction is conveniently carried out for one to several hours at room temperature.

Reaction (c) is performed in a suitable solvent such as dichloromethane in the presence of a suitable base such as $Et_3N$ at room temperature for one hour.

Reaction (d) is performed in a suitable solvent such as THF or DMF at room temperature for several hours with no base needed.

Reaction (e) is performed either in refluxing acetone or in DMF in the presence of a suitable base such as potassium carbonate and can conveniently be carried out at 80° C.

Reaction (f) is performed in a suitable solvent such as dichloromethane in the presence of a suitable base such as triethylamine and at room temperature for about 30 to 120 minutes.

Reaction (g) is performed in a suitable solvent such as acetonitril under reflux for 24 hours.

Reaction (h) is performed under different conditions depending on $R^1$; for example when $R^1$=$CF_3$ the reaction is performed in the presence of triethylamine in dichloromethane at −78° C. for 1 hour. For $R^1$=$NH_2$, the reaction is conducted in dioxane for 12 hours at reflux temperature. For $R^1$=$CH_3$ the reaction is conducted in dichloromethane at room temperature for 3 hours in the presence of triethylamine.

Reaction (i) is performed in a suitable solvent such as isopropanol at reflux temperature for 12-36 hours.

Reaction (j) is performed in a suitable solvent such as acetonitril at reflux temperature for 24 hours.

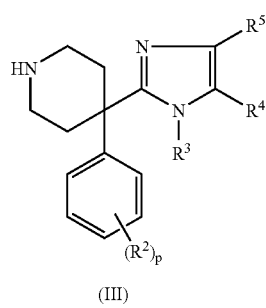

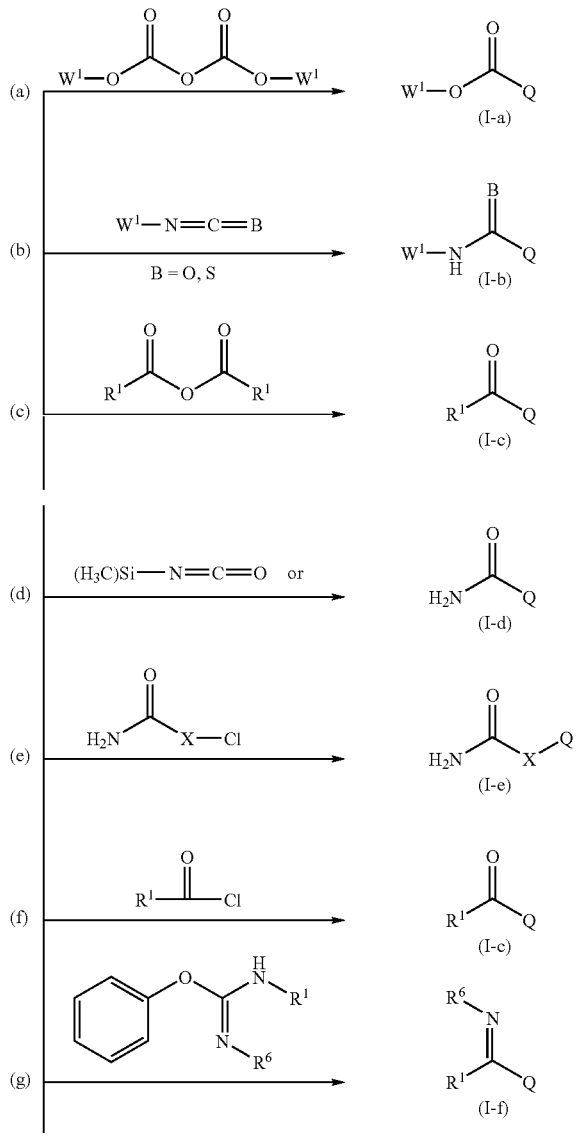

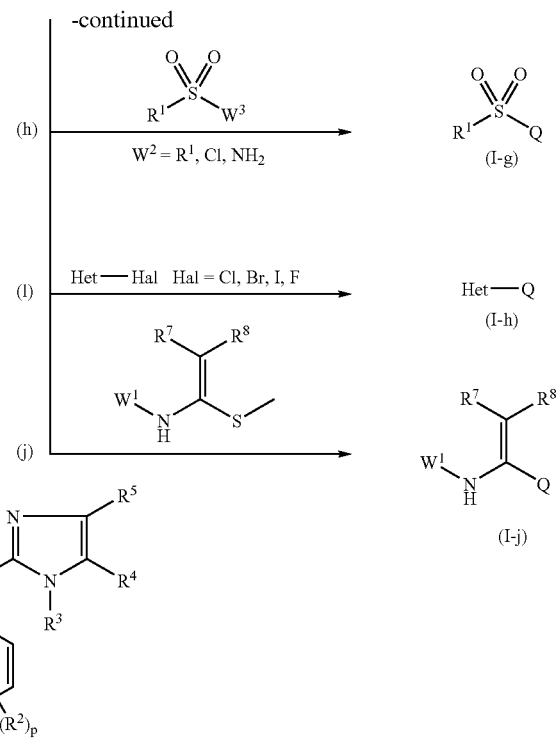

The compounds according to Formulas (I-c) can also be prepared by reacting an intermediate of Formula (IV) with an halide. In said reaction, all variables are defined as in Formula (I). The reaction is performed with a base such as NaH (60% in mineral oil) and in a reaction-inert solvent such as DMF or THF.

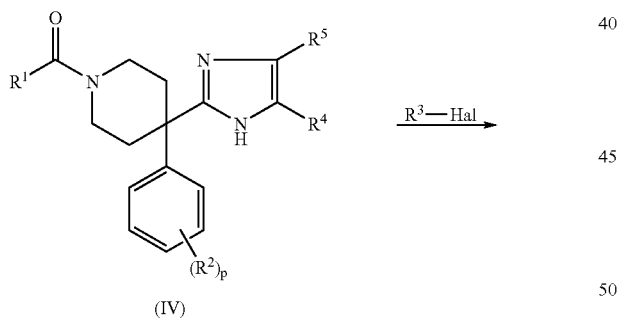

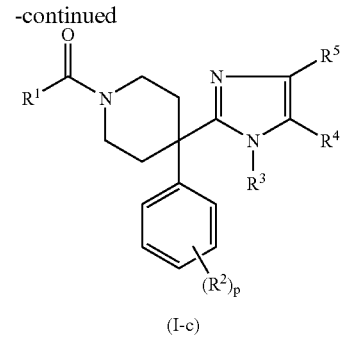

The starting material and the intermediate compounds according to Formulas (II), (III) and (IV) are compounds that are either commercially available or may be prepared according to conventional reaction procedures generally known in the art.

Intermediate compounds of Formula (II) may be prepared according to the following reaction scheme (4) wherein all variables are defined as in Formula (I):

Scheme 4

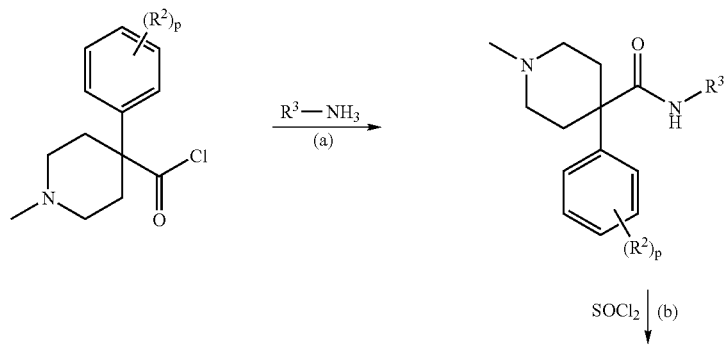

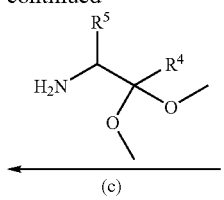
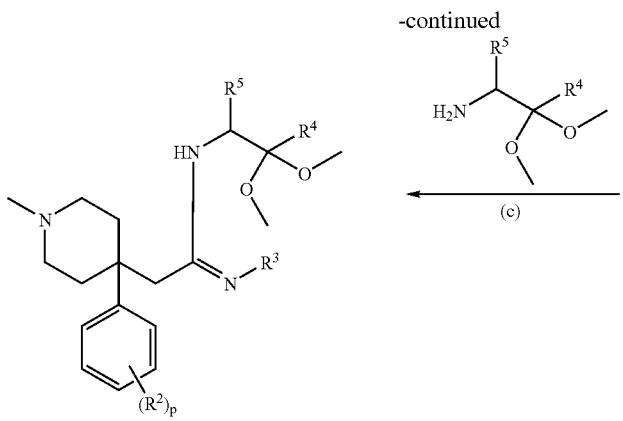
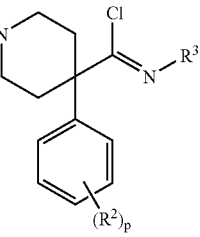

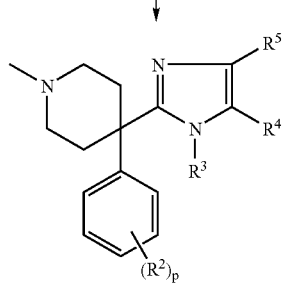

(II)

Reaction scheme 4 comprises the step (a) in which an acylchloride of the type shown is reacted with a substituted primary amine, e.g. benzylamine, in the presence of a suitable base, such as Et$_3$N and in a suitable reaction-inert solvent, such as dichloromethane. The reaction may conveniently carried out at room temperature.

In a next step (b), the adduct obtained in step (a) is refluxed with SOCl$_2$, after which the product obtained is reacted with appropriately substituted 2,2-dimethoxyethylamine in a reaction-inert solvent, such as DMF, for instance at room temperature (step c). In step (d) the adduct obtained in step (c) is cyclizised in HC to obtain the substituted imidazolyl-moiety.

Intermediate compounds of Formula (III) may be prepared from compounds according to Formula (I-c) by selectively reducing the alkyloxycarbonyl-moiety of the piperidinyl-moiety according to the following reaction:

-continued

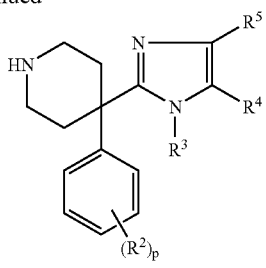

(III)

The reaction is performed in the presence of a suitable base, such as KOH, in a suitable reaction-inert solvent, such as 2-propanol and at reflux temperature.

Intermediate compounds according to Formula (IV) may be prepared by hydrogenating compounds according to Formula (I-c) according to the following reaction:

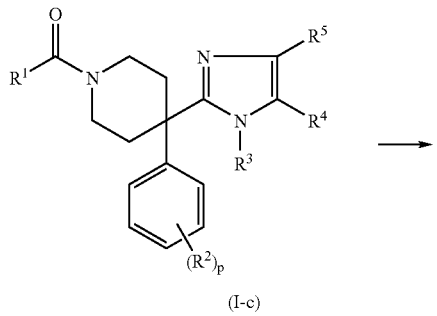

(I-c)

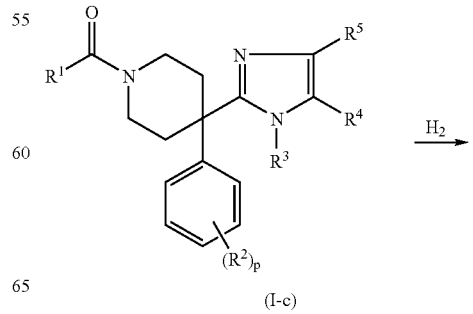

(I-c)

-continued

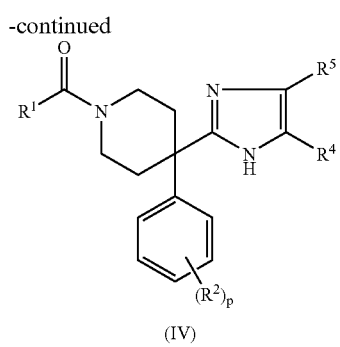

(IV)

wherein all variables are defined as in Formula (I). The reaction is performed in the is presence of a catalyst, such as Pd/C (10%) in methanol at a moderately elevated temperature.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC.

The following examples illustrate the present invention without being limited thereto.

Experimental Part

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The isolation method is described in detail below.

Hereinafter, "DMF" is defined as N,N-dimethylformamide, 'THF' is defined as tetrahydrofuran and "DIPE" is defined as diisopropyl ether.

A. Preparation of the Intermediate Compounds

EXAMPLE A1

1-Methyl-4-phenyl-4-piperidinecarbonyl chloride (0.49 mol) was added portionwise at room temperature to a stirring mixture of benzenemethanamine (0.49 mol) and N,N-diethylethanamine (1.223 mol) in $CH_2Cl_2$ (2500 ml). The mixture was stirred at room temperature for 1 hour. $K_2CO_3$ (150 g) and $H_2O$ were added. The mixture was stirred and separated into its layers. The aqueous layer was extracted with $CH_2Cl_2$. The combined organic layer was dried ($MgSO_4$), filtered and the solvent was evaporated. Yielding: 144 g (95%) of 1-methyl-4-phenyl-N-(phenylmethyl)-4-piperidinecarboxamide (interm. 1).

EXAMPLE A2

A mixture of intermediate 1 (0.47 mol) in $SOCl_2$ (750 ml) was stirred and refluxed for 1 hour. The solvent was evaporated. Toluene was added twice and evaporated again. Yielding: 190 g (100%) of N-[chloro(1-methyl4-phenyl-4-piperidinyl)methylene]-benzenemethanamine hydrochloride (interm. 2).

EXAMPLE A3

A mixture of intermediate 2 (0.47 mol) in DMF (750 ml) was cooled on an ice bath. 2,2-Dimethoxyethanamine (0.54 mol) dissolved in DMF was added dropwise. The mixture was stirred at room temperature overnight. The solvent was evaporated. Yielding: 210 g (100%) of N-(2,2-dimethoxyethyl)-1-methyl-4-phenyl-N'-(phenylmethyl)-4-piperidinecarboximidamide dihydrochloride (interm. 3).

EXAMPLE A4

A mixture of intermediate 3 (0.47 mol) in 6N HCl (1500 ml) was stirred until a cloudy solution, then washed with $CH_2Cl_2$ (900 ml), stirred at 80° C. for 1 hour, cooled, alkalized with a NaOH 50% solution and extracted with $CH_2Cl_2$. The organic layer was separated, dried ($MgSO_4$), filtered and the solvent was evaporated. The residue was crystallized from $CH_3CN$. The precipitate was filtered off and dried. Yielding: 38.3 g (25%) of 1-methyl-4-phenyl-4-[1-(phenylmethyl)-1H-imidazol-2-yl]piperidine (interm. 4).

EXAMPLE A5

A mixture of compound 1 (0.089 mol) in methanol (250 ml) was hydrogenated at 50° C. with Pd/C 10% (3 g) as a catalyst. After uptake of hydrogen (1 equiv.), the catalyst was filtered off and the filtrate was evaporated. The residue was crystallized from $CH_3CN$. The precipitate was filtered off and dried. Yielding: 23.89 g (90%) of ethyl 4-phenyl-4-(1H-imidazol-2-yl)-1-piperidinecarboxylate (interm. 5).

EXAMPLE A6

A mixture of intermediate 5 (0.026 mol) and KOH (0.26 mol) in 2-propanol (150 ml) was stirred and refluxed for 10 hours. The solvent was evaporated. The residue was taken up in $H_2O$ and the mixture was extracted with $CH_2Cl_2$. The organic layer was separated, dried, filtered and the solvent was evaporated. Yielding: 9.4 g of 4-phenyl-4-[1-(phenylmethyl)-1H-imidazol-2-yl]piperidine (interm. 6).

EXAMPLE A7

Reaction under $N_2$ atmosphere. A mixture of intermediate 5 (0.0033 mol) in DMF (5 ml) and THF (5 ml) was added dropwise to a solution of NaH, 60% in mineral oil (0.004 mol) in THF (10 ml), stirred at room temperature. The mixture was stirred for one hour at room temperature. Then, a solution of 4-(acetyloxy)benzenemethanol (0.004 mol) in THF was added dropwise and the resulting reaction mixture was extracted with $CH_2Cl_2$. The separated organic layer was dried ($Na_2SO_4$), filtered and the solvent was evaporated. The residue was purified by short open column chromatography over silica gel (eluent: $CH_2Cl_2/(CH_3OH/NH_3)$ 95/5). The pure fractions were collected and the solvent was evaporated. Yielding: 1.33 g of ethyl 4-phenyl-4-[1-((4-methylcarboxy)phenylmethyl)-1H-imidazol-2-yl]-1-piperidinecarboxylate (interm. 7).

B. Preparation of the Final Compounds

EXAMPLE B1

A mixture of intermediate 4 (0.05 mol) and N,N-diethylethanamine (0.15 mol) in toluene (750 ml) was stirred at 100° C. Ethyl chloroformate (0.25 mol) was added dropwise and the reaction mixture was stirred and refluxed for 1 hour and then cooled. The mixture was poured out into an aqueous $K_2CO_3$ solution (35 g $K_2CO_3$). The layers were separated. The water layer was extracted with $CH_2Cl_2$. The separated organic layer was dried ($MgSO_4$), filtered and the solvent evaporated. The residue was purified over silica gel on a glass filter (eluent: $CH_2Cl_2/C_2H_5OH$ 98/2). The desired fractions were collected and the solvent was evaporated. The residue was crystallized from $CH_3CN$, filtered off and dried. Yielding: 16.7 g (86%) of ethyl 4-phenyl-4-[1-(phenylmethyl)-1H-imidazol-2-yl]-1-piperidinecarboxylate (compound 1).

EXAMPLE B2

The preparation of compound 2

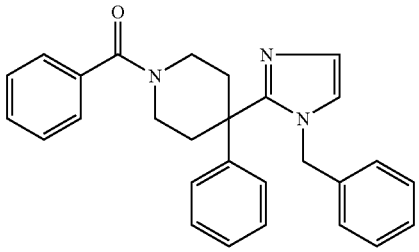

Benzoyl chloride (0.0023 mol) was added to a mixture of intermediate 6 (0.0019 mol) and N,N-diethylethanamine (0.0024 mol) in $CH_2Cl_2$ (15 ml), stirred at room temperature. The reaction mixture was stirred for 30 min at room temperature. Water was added. The layers were separated. The aqueous layer was extracted with $CH_2Cl_2$. The combined organic layers were dried ($Na_2SO_4$), filtered and the solvent evaporated.

The residue was purified by short open column chromatography over silica gel (eluent: $CH_2Cl_2/(CH_3OH/NH_3)$ 98/2). The pure fractions were collected and the solvent was evaporated. The residue was recrystallized from n-hexane, filtered off and dried. Yield: 0.42 g (52%) of compound 2; m.p. 122.7° C.

EXAMPLE B3

The preparation of compound 3

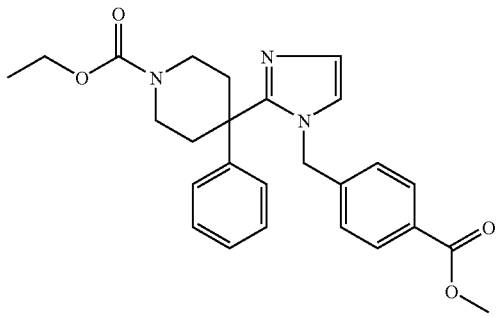

Reaction under $N_2$ atmosphere. A solution of intermediate 5 (0.0054 mol) in DMF (10 ml) and THF (10 ml) was added dropwise to NaH (0.00624 mol) in THF (30 ml) and the mixture was stirred at room temperature for 1 hour. Then, methyl 4-(bromomethyl)-benzoate (0.00624 mol) in THF (5 ml) was added dropwise and the reaction mixture was stirred at 60° C. for 3 hours. Water was added and the mixture was extracted with $CH_2Cl_2$. The combined organic layers were dried ($Na_2SO_4$), filtered and the solvent was evaporated. The residue was purified by short open column chromatography over silica gel (eluent: $CH_2Cl_2(CH_3OH/NH_3)$ 98/2). The desired fractions were collected and the solvent was evaporated. The residue was crystallized from DIPE, filtered off and dried. Yield: 1.7 g (70%) of compound 3; m.p. 149.1° C.

EXAMPLE B4

The preparation of compound 4

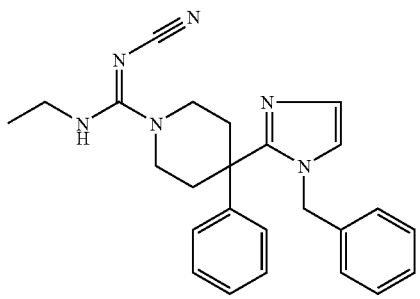

A mixture of intermediate 6 (0.0059 mol) and

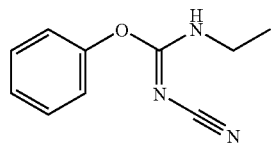

(0.0059 mol) in $CH_3CN$ (70 ml) was stirred and refluxed for 24 hours. The solvent was evaporated. Water was added. This mixture was extracted with $CH_2Cl_2$. The separated organic layer was dried ($Na_2SO_4$, anhydrous), filtered and the solvent was evaporated. The residue was crystallized from DIPE, filtered off and recrystallized from $CH_3CN$, filtered off and dried. Yield: 0.33 g of compound 4; m.p. 84.2° C.

EXAMPLE B5

The preparation of compound 5

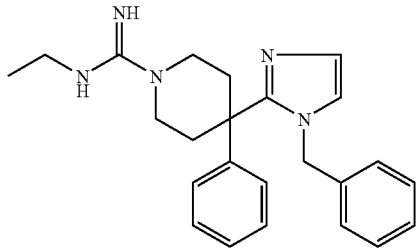

A mixture of compound 4 (0.0001 mol) in HCl 6N (22.8 ml) was stirred and refluxed for 4 hours. The reaction mixture was alkalized, then extracted with $CH_2Cl_2$. The separated organic layer was dried ($Na_2SO_4$, anhydrous), filtered and the solvent was evaporated. The residue was recrystallized from DIPE, filtered off and dried. Yield: 0.24 g (62%) of compound 5.

EXAMPLE B6

The preparation of compound 6

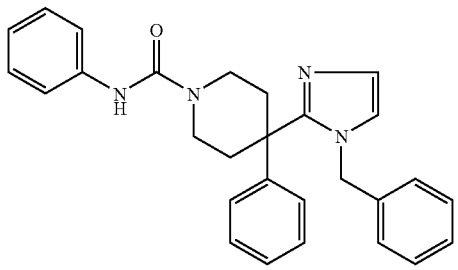

Isocyanatobenzene (0.0094 mol) was added dropwise to intermediate 6 (0.0094 mol) in THF (50 ml) and the reaction mixture was stirred for 30 min at room temperature. Water was added and this mixture was extracted with CH$_2$Cl$_2$. The separated organic layer was dried (Na$_2$SO$_4$), filtered and the solvent evaporated. The solid residue was washed with 2-propanone, filtered off and dried. Yield: 2.7 g (68%) of compound 6.

EXAMPLE B7

The preparation of compound 7

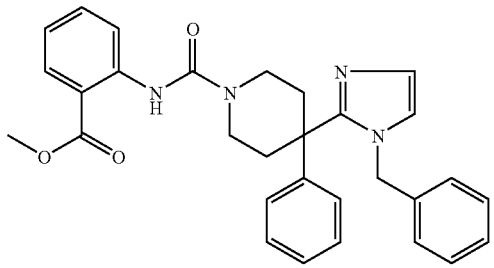

Methyl 2-isocyanatobenzoate (0.0007 mol) was added to intermediate 6 (0.0007 mol) in THF (10 ml) and the reaction mixture was stirred for 3 hours at room temperature. Water was added and this mixture was extracted with CH$_2$Cl$_2$. The separated organic layer was dried (Na$_2$SO$_4$), filtered and the solvent evaporated. The residue (0.4 g) was purified by HPLC over silica gel (eluent: CH$_2$Cl$_2$/CH$_3$OH 98/2). The desired fractions were collected and the solvent was evaporated. Yield: 0.2 g (66%) of compound 7.

EXAMPLE B8 a) The preparation of compound 8

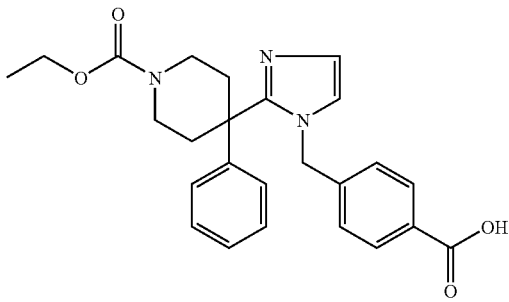

A mixture of compound 3 (0.002 mol) and LiOH (0.02 mol) in THF (11 ml) and H$_2$O (11 ml) was stirred at room temperature for 24 hours. H$_2$O was added. The mixture was brought to pH 6 and then extracted with CH$_2$Cl$_2$. The organic layer was separated, dried, filtered and the solvent was evaporated. The residue was washed with CH$_2$Cl$_2$. Yielding: 0.72 g (83%) of compound 8; m.p. 251.6° C.

b) The preparation of compound 9

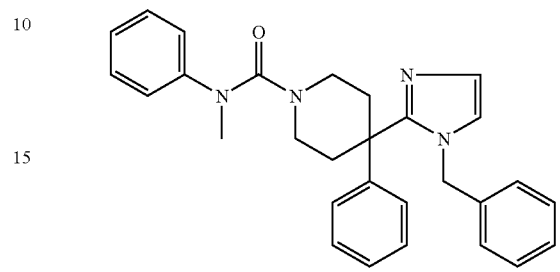

Reaction under N$_2$ atmosphere. A solution of NaH 60% (0.000642 mol) in DMF (2 ml) was stirred at room temperature. A solution of compound 6 (0.000642 mol) in DMF (8 ml) was added dropwise and the reaction mixture was stirred for one hour at room temperature. CH$_3$I (0.001284 mol) was added and the reaction mixture was stirred at 60° C. in a Parr pressure vessel for 2 hours. The solvent was evaporated. The residue was purified by high-performance liquid chromatography over silica gel (eluent: CH$_2$Cl$_2$/CH$_3$OH 98/2). The desired fractions were collected and the solvent was evaporated. Yield: 0.14 g (49%) of compound 9.

c) The preparation of compound 10

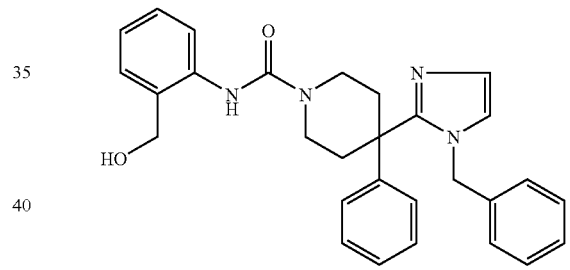

LiAlH$_4$ 1M in THF (0.000444 mol) was added dropwise to a solution of compound 7 (0.000404 mol) in THF (5 ml), stirred at 0° C. The reaction mixture was stirred for 30 min at 0° C. The mixture was treated with a 10% aqueous NH$_4$Cl solution and extracted with EtOAc. The separated organic layer was dried (Na$_2$SO$_4$), filtered and the solvent evaporated. The residue was purified by CC-TLC on Chromatotron (eluent: CH$_2$Cl$_2$/CH$_3$OH 96/4). The desired fractions were collected and the solvent was evaporated. The residue was crystallized from CH$_3$OH/H$_2$O, filtered off and dried. Yield: 0.020 g (10%) of compound 10.

d) The preparation of compound 11

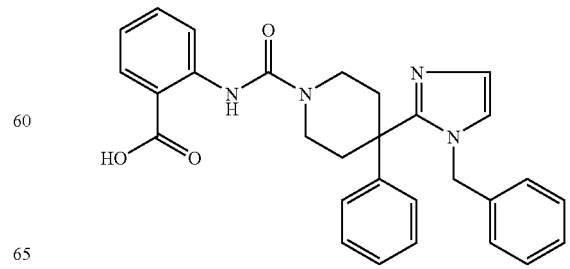

LiOH (0.001423 mol) was added portionwise to a solution of compound 7 (0.0006469 mol) in dixoane/H₂O 1/1 (6 ml). The resulting suspension was stirred for 18 hours at room temperature. The solvent was evaporated. The residue was taken up into water and extracted with a mixture of EtOAc and 1-butanol. The organic layer was separated, dried (Na₂SO₄), filtered and the solvent was evaporated. The residue was taken up into 1 N HCl, then extracted with EtOAc. The organic layer was separated, washed with brine, dried (Na₂SO₄), filtered and the solvent was evaporated. The residue was crystallized from Et₂O/CH₂Cl₂, filtered off and dried. Yield: 0.16 g (51%) of compound 11.

EXAMPLE B9

LiOH (0.018 mol) was added to a mixture of intermediate 7 (0.0018 mol) in THF (10 ml) and H₂O (10 ml). The reaction mixture was stirred for 3 hours at room temperature. Water was added. CH₂Cl₂ was added. The reaction mixture was extracted. The organic layer was separated, dried (Na₂SO₄), filtered and the solvent was evaporated. The white solid residue was washed with methanol and CH₂Cl₂, then dried. Yielding: 0.54 g of ethyl 4-phenyl-4-[1-(4-hydroxyphenylmethyl)-1H-imidazol-2-yl]-1-piperidinecarboxylate (compound 12).

The following compounds as listed in Tables 1-5 were prepared:

TABLE 1

| Comp. nr. | Exp. nr. | R¹ | R³ | Phys. prop. |
|---|---|---|---|---|
| 110 | B2 | —H | phenylmethyl | |
| 13 | B1 | methoxy | phenylmethyl | |
| 14 | B3 | ethoxy | cyclohexylmethyl | m.p. = 137 |
| 1 | B1 | ethoxy | phenylmethyl | |
| 12 | B9 | ethoxy | 4-hydroxyphenylmethyl | |
| 15 | B3 | ethoxy | 4-methoxyphenylmethyl | |
| 16 | B3 | ethoxy | 4-fluorophenylmethyl | m.p. = 117 |

TABLE 1-continued
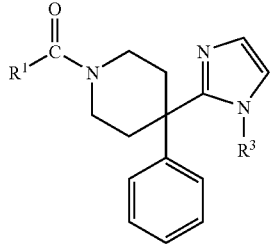
| Comp. nr. | Exp. nr. | R¹---- | R³---- | Phys. prop. |
|---|---|---|---|---|
| 17 | B3 |  | 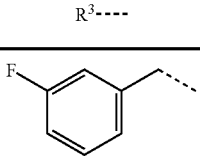 | m.p. = 127 |
| 18 | B3 | 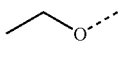 | 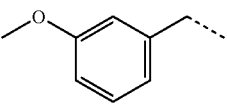 | m.p. = 125 |
| 8 | B6 | 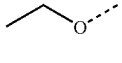 |  | m.p. = 252 |
| 3 | B3 | 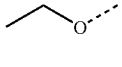 | 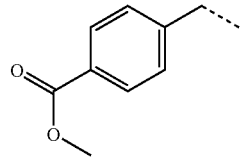 | m.p. = 149 |
| 19 | B3 | 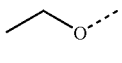 | 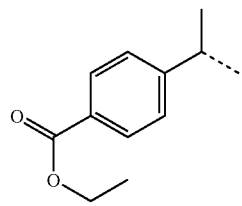 | |
| 20 | B3 | 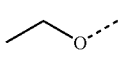 | 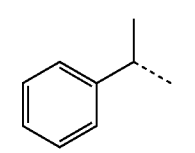 | |
| 21 | B3 | 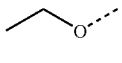 | 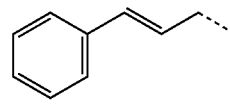 | |
| 22 | B3 | 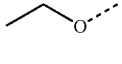 | 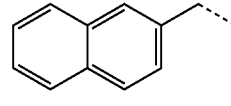 | |
| 23 | B3 | 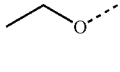 | 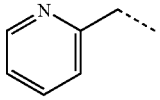 | m.p. = 199 |

TABLE 1-continued

| Comp. nr. | Exp. nr. | R¹---- | R³---- | Phys. prop. |
|---|---|---|---|---|
| 112 | B3 | ethoxy | 5-methyl-isoxazol-3-ylmethyl | m.p. = 128 |
| 24 | B1 | propoxy | benzyl | m.p. = 130 |
| 25 | B1 | isopropoxy | benzyl | m.p. = 160 |
| 26 | B2 | tert-butoxy | benzyl | m.p. = 133 |
| 27 | B1 | butoxy | benzyl | m.p. = 80 |
| 28 | B1 | cyclohexyloxy | benzyl | m.p. = 215 |
| 29 | B2 | methoxy | benzyl | m.p. = 111 |
| 30 | B3 | methoxy | 4-(methoxycarbonyl)benzyl | |
| 31 | B3 | methoxy | 2-isopropylbenzyl | |
| 32 | B1 | benzyloxy | benzyl | |

TABLE 1-continued
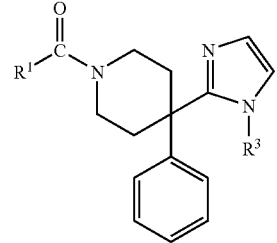
| Comp. nr. | Exp. nr. | R¹---- | R³---- | Phys. prop. |
|---|---|---|---|---|
| 33 | B2 | CH₃---- | 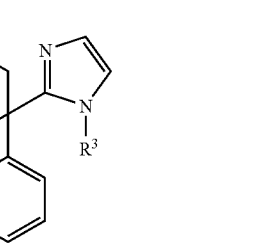 | m.p. = 183 |
| 34 | B2 | CH₃CH₂---- | 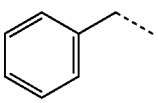 | m.p. = 133 |
| 35 | B2 | isopropyl----- | 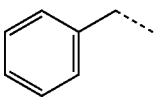 | m.p. = 107 |
| 36 | B2 | 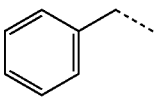 |  | m.p. = 111 |
| 37 | B2 | tert-butyl----- | 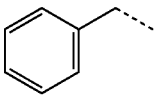 | m.p. = 165 |
| 2 | B2 | 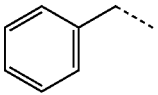 | 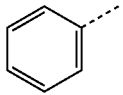 | m.p. = 123 |
| 38 | B3 | 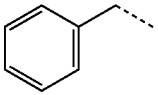 | 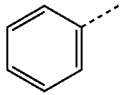 | |
| 39 | B3 | 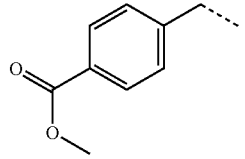 | 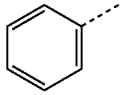 | |
| 40 | B3 | 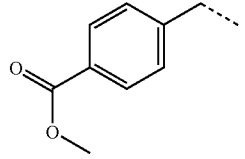 | 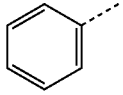 | |

TABLE 1-continued
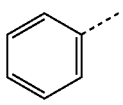
| Comp. nr. | Exp. nr. | R¹---- | R³---- | Phys. prop. |
|---|---|---|---|---|
| 41 | B3 | 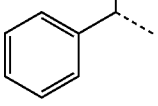 | 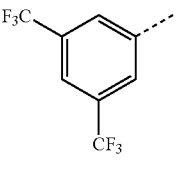 | |
| 42 | B2 | 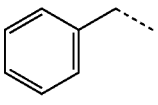 | 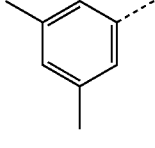 | m.p. = 151 |
| 43 | B2 | 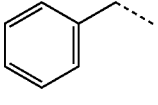 | 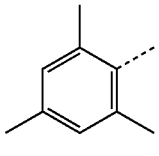 | m.p. = 79 |
| 44 | B2 | 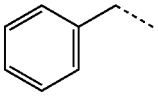 | 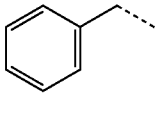 | m.p. = 149 |
| 45 | B2 | 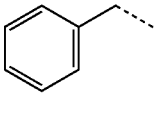 | 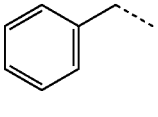 | |
| 46 | B2 | NH₂---- | 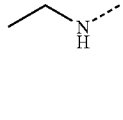 | m.p. = 208 |
| 47 | B2 | 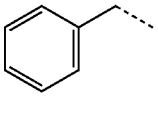 | 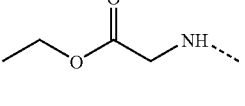 | m.p. = 144 |
| 48 | B2 | 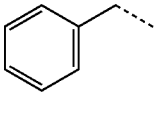 | 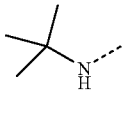 | |
| 49 | B2 | 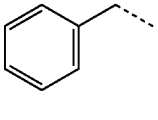 | | |

TABLE 1-continued

| Comp. nr. | Exp. nr. | R¹---- | R³---- | Phys. prop. |
|---|---|---|---|---|
| 50 | B2 | butyl-NH- | benzyl- | |
| 51 | B2 | cyclohexyl-NH- | benzyl- | |
| 6 | B6 | phenyl-NH- | benzyl- | |
| 52 | B3 | phenyl-NH- | 4-(methoxycarbonyl)benzyl- | |
| 53 | B3 | phenyl-NH- | naphthalen-2-ylmethyl- | |
| 54 | B3 | phenyl-NH- | cyclohexylmethyl- | |
| 55 | B3 | phenyl-NH- | 2-isopropylphenyl- (alpha-methylbenzyl) | |
| 56 | B3 | phenyl-NH- | 2-fluorobenzyl- | |
| 57 | B3 | phenyl-NH- | 3-methoxybenzyl- | |

TABLE 1-continued

| Comp. nr. | Exp. nr. | R¹--- | R³--- | Phys. prop. |
|---|---|---|---|---|
| 58 | B3 | phenyl-NH- | 3-fluorophenyl-CH₂- | |
| 59 | B3 | phenyl-NH- | pyridin-2-yl-CH₂- | |
| 60 | B3 | phenyl-NH- | phenyl-C(=O)- | |
| 61 | B3 | phenyl-NH- | 4-(methylsulfonyl)phenyl-CH₂- | |
| 62 | B3 | phenyl-NH- | 4-fluorophenyl-CH₂- | |
| 63 | B3 | phenyl-NH- | 5-methylisoxazol-3-yl-CH₂- | |
| 64 | B2 | 2-fluorophenyl-NH- | phenyl-CH₂- | |
| 65 | B2 | 2-chlorophenyl-NH- | phenyl-CH₂- | |
| 66 | B2 | 2-bromophenyl-NH- | phenyl-CH₂- | |

TABLE 1-continued

| Comp. nr. | Exp. nr. | R¹---- | R³---- | Phys. prop. |
|---|---|---|---|---|
| 67 | B2 | 2-methoxyphenyl-NH- | benzyl | |
| 68 | B2 | 2,6-dimethylphenyl-NH- | benzyl | |
| 7 | B7 | 2-(methoxycarbonyl)phenyl-NH- | benzyl | |
| 69 | B2 | 3-methoxyphenyl-NH- | benzyl | |
| 7 | B2 | 4-methoxyphenyl-NH- | benzyl | |
| 70 | B2 | 2-ethoxyphenyl-NH- | benzyl | |
| 71 | B2 | 4-nitrophenyl-NH- | benzyl | |
| 72 | B2 | 3-fluorophenyl-NH- | benzyl | |

TABLE 1-continued
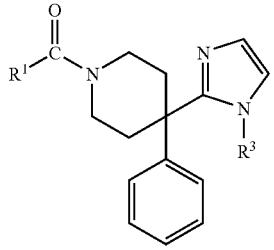
| Comp. nr. | Exp. nr. | R¹---- | R³---- | Phys. prop. |
|---|---|---|---|---|
| 73 | B2 | 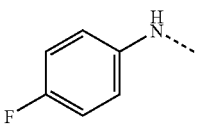 | 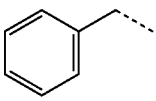 | |
| 74 | B2 | 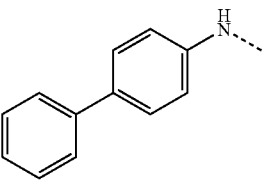 | 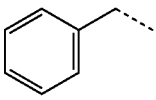 | |
| 10 | B6 | 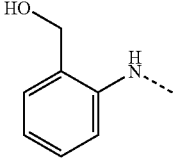 | 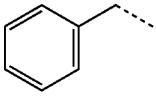 | |
| 75 | B2 | 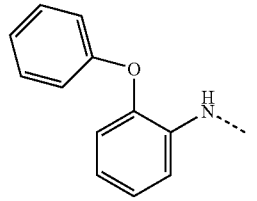 | 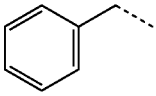 | |
| 76 | B2 | 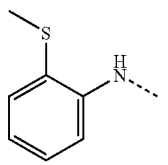 | 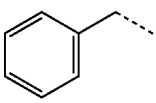 | |
| 77 | B2 | 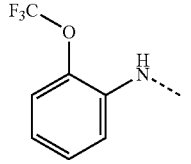 | 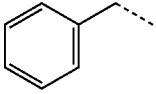 | |
| 11 | B6 | 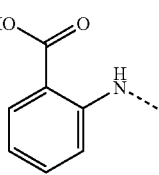 | 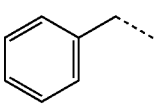 | |

TABLE 1-continued

| Comp. nr. | Exp. nr. | R¹---- | R³---- | Phys. prop. |
|---|---|---|---|---|
| 78 | B2 | 2-methoxy-5-chloroanilino | benzyl | |
| 79 | B2 | 2,4-dimethoxyanilino | benzyl | |
| 9 | B6 | N-methyl-N-phenylamino | benzyl | |
| 80 | B2 | benzylamino | benzyl | |
| 81 | B2 | naphthalen-2-ylamino | benzyl | |
| 113 | B2 | naphthalen-1-ylamino | benzyl | |
| 82 | B2 | 4-methylpiperazin-1-yl | benzyl | |
| 83 | B2 | 2-methyl-1-(cyclopropylmethyl)pyrrolidinyl | benzyl | m.p. = 74 |

TABLE 1-continued
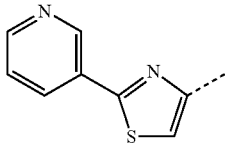
| Comp. nr. | Exp. nr. | R¹---- | R³---- | Phys. prop. |
|---|---|---|---|---|
| 84 | B2 | 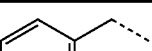 | 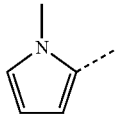 | |
| 85 | B2 | 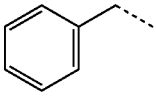 | 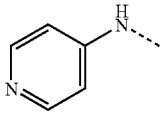 | m.p. = 165 |
| 86 | B2 | 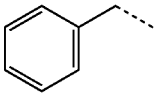 | 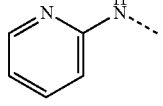 | |
| 87 | B2 | 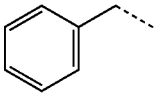 | 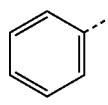 | |
TABLE 2
| Comp. nr. | Exp. nr. | Rᵃ---- | Rᵇ---- | R²---- | Position of R² | Phys. data |
|---|---|---|---|---|---|---|
| 88 | B3 | 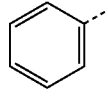 | H | —O--- | c | |
| 89 | B3 | 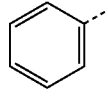 | H | ----F | c | |

TABLE 2-continued

| Comp. nr. | Exp. nr. | Rᵃ | Rᵇ | R² | Position of R² | Phys. data |
|---|---|---|---|---|---|---|
| 90 | B3 | phenyl | H | F | a | |
| 114 | B3 | phenyl | phenyl | — | — | |
| 115 | B3 | phenyl | H | — | — | |

TABLE 3

| Comp. nr. | Exp. nr. | A=B | R¹ | Phys. data |
|---|---|---|---|---|
| 5 | B5 | C=NH | ethyl-NH | |
| 91 | B5 | C=N—H | phenyl-NH | |
| 4 | B4 | C=N—CN | ethyl-NH | m.p. = 84 |
| 92 | B4 | C=N—CN | phenyl-NH | |
| 93 | B4 | C=C—NO₂ | phenyl-NH | |
| 95 | B2 | C=S | ethyl-NH | m.p. = 172 |
| 96 | B2 | C=S | phenyl-NH | |
| 94 | B2 | SO₂ | CH₃ | m.p. = 167 |
| 97 | B2 | SO₂ | NH₂ | m.p. = 212 |

TABLE 3-continued
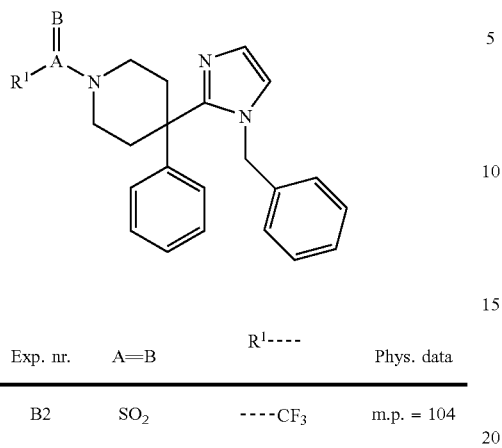
| Comp. nr. | Exp. nr. | A=B | R¹---- | Phys. data |
|---|---|---|---|---|
| 111 | B2 | SO$_2$ | ----CF$_3$ | m.p. = 104 |
| 98 | B2 | SO$_2$ | ![phenylamino] | |
TABLE 4
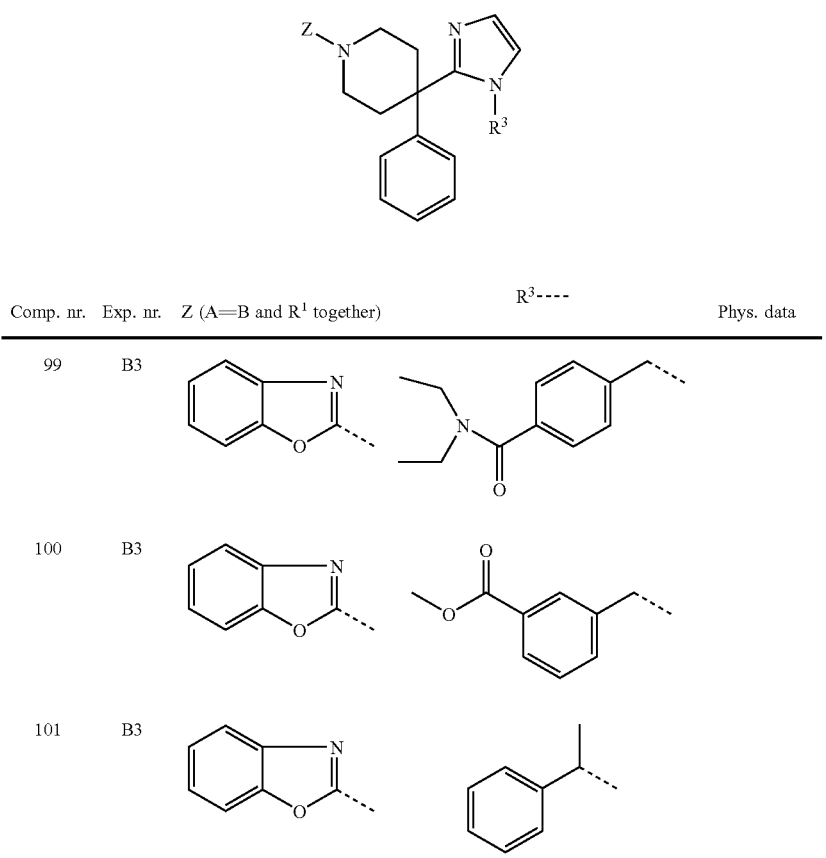
| Comp. nr. | Exp. nr. | Z (A=B and R¹ together) | R³---- | Phys. data |
|---|---|---|---|---|
| 99 | B3 | benzoxazol-2-yl | 4-(N,N-diethylcarbamoyl)benzyl | |
| 100 | B3 | benzoxazol-2-yl | 3-(methoxycarbonyl)benzyl | |
| 101 | B3 | benzoxazol-2-yl | 1-phenylethyl | |

TABLE 4-continued

| Comp. nr. | Exp. nr. | Z (A=B and R¹ together) | R³---- | Phys. data |
|---|---|---|---|---|
| 102 | B3 | benzoxazol-2-yl | 4-(methoxycarbonyl)benzyl | |
| 103 | B2 | pyrimidin-2-yl | benzyl | m.p. = 204 |
| 104 | B2 | 1-methylbenzimidazol-2-yl | benzyl | m.p. = 181 |
| 105 | B2 | thiazol-2-yl | benzyl | m.p. = 190 |
| 106 | B2 | benzothiazol-2-yl | benzyl | m.p. = 107 |

TABLE 5

| Comp. nr. | Exp. nr. | R¹---- | Phys. data |
|---|---|---|---|
| 107 | B3 | ----OH | |
| 108 | B2 | ----N(ethyl)₂ | m.p. = 105 |
| 109 | B2 | ----NH₂ | m.p. = 136 |

B. Pharmacological Examples

The pharmacological properties were examined for radioligand binding as well as GTPγS binding assays, of the selected compounds on the cloned human δ, κ and μ opioid receptors, expressed in a mammalian cell line. Second messenger signaling was measured on membrane preparations via stimulation of [$^{35}$S]GTPγS binding. In this functional assay, agonistic and antagonistic properties of the compounds were investigated.

DPDPE ((D-Pen$^{2,5}$)enkephalin) was used as the reference agonist and naltrindole as the reference antagonist for the δ opioid receptor (Malatynska E, Wang Y, Knapp R J, Santoro G., LiX, Waite S., Roeske W R, Yamamura H. I.: *Human δ opioid receptor: a stable cell line for functional studies of opioids. NeuroReport* 6, 613-616, 1995) and (Portoghese P. S., Sultana M, Takemori A. E.: *Naltrindole, a highly selective and potent non-peptide δ opioid receptor antagonist. Eur. J. Pharmacol.* 146, 185-186, 1988) and U69593 and nor-binaltorphimine (nor-BNI) were used for the κ opioid receptor as the reference agonist and antagonist, respectively. For the μ opioid receptor, morphine was used as the reference agonist and naloxone as the reference antagonist (Alt A., Mansour A., Akil H., Medzihradsky F., Traynor J. R., Woods J. H.: *Stimulation of guanosine-5'-O-(3-[$^{35}$S]thio) triphosphate binding by endogenous opioids acting at a* cloned Mu receptor. *J. Pharmacol. Exp. Ther.* 286, 282-288, 1998) and (Smart D., Hirst R. A., Hirota K, Grandy D. K., Lambert D. G.: *The effects of recombinant rat μ-opioid receptor activation in CHO cells on phospholipase C, [Ca$^{2+}$]I and adenylyl cyclase.* Br. J. Pharmacol. 120, 1165-1171, 1997).

Materials and Methods

Cell Culture

CHO cells, permanent transfected with the κ or μ opioid receptor, were cultured in Dulbecco's modified Eagle's medium (DMEM)/Nutrient mixture Ham's F12 (ratio 1:1) supplemented with 10% heat inactivated fetal calf serum, and an antibiotic solution containing 100 IU/ml penicillin G, 100 μg/ml streptomycin sulfate, 110 μg/ml pyruvic acid and 300 μg/ml L-glutamine. C6 glioma cells, permanent transfected with the δ opioid receptor, required a DMEM medium, enriched with 10% heat inactivated fetal calf serum and the antibiotic solution as described above.

Membrane Preparation

The membranes were prepared as total particulate fractions. All cell lines were cultured to 90% confluency on 145 mm Petri dishes and treated with 5 mM sodium butyrate, 24 hours before collection. The culturing medium was removed and the cells were washed with ice cold phosphate buffered saline (PBS w/o Ca$^{2+}$ and Mg$^{2+}$), scraped from the plates in 50 mM Tris-HCl buffer, pH 7.4, and collected through centrifugation (10 minutes at 16,000 RPM at 4° C.). The cell pellet was re-suspended in hypotonic 5 mM Tris-HCl buffer, pH 7.4, and re-homogenized with an Ultra Turrax homogenizer. The homogenate was centrifuged at 18000 RPM for 20 minutes at 4° C. The final pellet was re-suspended in 50 mM Tris-HCl buffer, pH 7.4 and stored in aliquots at −70° C.

A protein determination was performed using the Biorad protein assay (Bradford) using bovine serum albumine (13SA) as a standard (Bradford, M. M.: *A rapid and sensitive method for the quantification of microgram quantities of protein utilizing the principle of protein-dye binding. Analytical Biochem .* 72: 248-254, 1976).

Radioligand Binding

Preliminary radioligand binding experiments were carried out to reveal the optimal assay conditions for these opioid receptor subtypes in their corresponding mammalian cell membranes.

Competitive inhibition of [$^3$H]DPDPE by the compounds was performed with a concentration of the radioligand of 2 nM (K$_d$=1.7 nM) and various concentrations in singlet of the compounds, spanning at least 3 orders of magnitude around the pIC$_{50}$ value. For competition binding on the κ and μ receptor, [$^3$H]U69593 (K$_d$=0.4 nM) and [$^3$H]DAMGO (K$_d$=0.6 nM) were used respectively at a concentration of 1 nM. Membranes were thawed on ice and diluted in a 50 mM Tris-HCl buffer, pH 7.4. For the δ opioid receptor, this incubation buffer was supplemented with 2 mM MgCl$_2$, 1 mM EGTA and 0.1% BSA. Non-specific binding was defined in the presence of 1 μM of naltrindole, spiradoline and dextromoramide for the δ, κ, and μ opioid receptor, respectively. An incubation of 1 hour at 25° C. was found to be optimal for competition binding assays for all the three receptor subtypes. The assays were carried out in a final volume of 500 μl. The reaction was terminated by rapid filtration over an UniFilter™-96, GF/B™ under reduced pressure using Filtermate 196 (Packard). The amount of bound radioactivity on the filter unit was determined after filter drying and scintillant addition (Microscint-O; Packard) by liquid scintillation counting.

[$^{35}$S]GTPγS Binding

Determination of [$^{35}$S]GTPγS binding to the G-proteins was carried out with a modified procedure of Lazareno (Lazareno S.: *Measurement of agonist-stimulated[$^{35}$S] GTPγS binding to cell membranes. Meth. Molec. Biol.* 106, 231-243, 1999).

In preliminary [$^{35}$S]GTPγS binding experiments, assay conditions were optimized which resulted in the choice of the following buffers: 20 mM Hepes with 100 mM NaCl, containing 3 μM GDP and 1 mM MgCl$_2$ for the μ opioid receptor CHO membranes, containing 10 μM GDP and 1 mM MgCl$_2$ for the δ opioid receptor C6 glioma cell membranes, and 10 μM GDP and 0.3 mM MgCl$_2$ for the κ opioid receptor CHO membranes. The assay mixtures contained 10 μg of membrane protein. An additional 10 μg/ml saponine was added to the diluted membranes as a detergent to maximize the [$^{35}$S]GTPγS penetration through the membranes.

For testing agonistic activity, 175 μl of diluted membranes was pre-incubated in the buffer described above together with 25 μl of buffer and 25 μl of varying concentrations of the compound in a total volume of 225 μl. For antagonistic activities, the 25 μl of the buffer addition was replaced with the reference agonist for stimulating the basal levels. For all three cell lines, a concentration of 300 nM of DPDPE, U69593 and morphine were used for their corresponding receptor subtypes. After a 20 minutes pre-incubation period at 37° C., 25 μl of [$^{35}$S]GTPγS was added to a final concentration of 0.25 nM and the assay mixtures were further incubated for 20 minutes at 37° C. Bound and free [$^{35}$S]GTPγS were separated by rapid filtration over an UniFilter™-96, GF/B™ under reduced pressure using Filtermate 196 (Packard). The amount of bound radioactivity on the filter unit was determined after filter drying and scintillant addition (Microscint-O; Packard) by liquid scintillation counting.

Basal [$^{35}$S]GTPγS binding was measured in absence of compounds. Stimulation by agonist was calculated as the percentage increase above basal levels. The sigmoid agonist concentration response curves for increases in [$^{35}$S]GTPγS binding and antagonist inhibition curves for inhibition of the reference agonist-stimulated [$^{35}$S]GTPγS binding were analyzed by non-linear regression using the GraphPad Prism program. Data were retrieved from independent experiments and the different concentration points were run in duplicates.

All compounds according to the invention showed a pIC$_{50}$ value of at least 6 for the delta opioid receptor and a pIC$_{50}$ value of 6 or less for either mu and kappa receptor.

The compounds listed in Table 6 showed a pIC$_{50}$ value of between 7 and 8 for the delta opioid receptor and a pIC$_{50}$ value of 6 or less for either mu and kappa receptor.

The compounds listed in Table 7 showed a pIC$_{50}$ value above 8 for the delta opioid receptor and a pIC$_{50}$ value of 6 or less for either mu and kappa receptor. The selectivity for the delta opioid receptor over the mu opioid receptor is as high as 600.

TABLE 6 pIC$_{50}$ values for the delta opioid receptor agonist test.

| Comp. Nr. | pIC$_{50}$ | Comp. Nr. | pIC$_{50}$ |
|---|---|---|---|
| 43 | 7.9 | 22 | 7.3 |
| 17 | 7.9 | 87 | 7.3 |

TABLE 6-continued pIC$_{50}$ values for the delta opioid receptor agonist test.

| Comp. Nr. | pIC$_{50}$ | Comp. Nr. | pIC$_{50}$ |
|---|---|---|---|
| 30 | 7.9 | 45 | 7.3 |
| 105 | 7.9 | 51 | 7.3 |
| 78 | 7.9 | 4 | 7.3 |
| 101 | 7.8 | 55 | 7.3 |
| 28 | 7.8 | 71 | 7.3 |
| 11 | 7.8 | 99 | 7.3 |
| 29 | 7.8 | 34 | 7.2 |
| 67 | 7.8 | 72 | 7.2 |
| 7 | 7.7 | 81 | 7.2 |
| 9 | 7.7 | 64 | 7.2 |
| 52 | 7.7 | 18 | 7.2 |
| 103 | 7.7 | 42 | 7.2 |
| 26 | 7.7 | 10 | 7.2 |
| 27 | 7.7 | 33 | 7.1 |
| 15 | 7.6 | 37 | 7.1 |
| 69 | 7.6 | 80 | 7.1 |
| 50 | 7.6 | 90 | 7.1 |
| 32 | 7.6 | 56 | 7.1 |
| 93 | 7.5 | 47 | 7.1 |
| 65 | 7.5 | 43 | 7.1 |
| 84 | 7.5 | 48 | 7.1 |
| 66 | 7.5 | 79 | 7.0 |
| 75 | 7.4 | 111 | 7.0 |
| 13 | 7.4 | 7 | 7.0 |
| 76 | 7.4 | 68 | 7.0 |
| 96 | 7.4 | 95 | 7.0 |
| 94 | 7.4 | 92 | 7.0 |
| 70 | 7.4 | 49 | 7.0 |
| 36 | 7.3 | 74 | 7.0 |

TABLE 7

Results for the agonist receptor binding (pIC$_{50}$) and signal transport binding (pIC$_{50}$) testing.

| Comp. Nr. | Formula | Agonist receptor binding (pIC$_{50}$) | | | Signal transport binding (pIC$_{50}$) | |
|---|---|---|---|---|---|---|
| | | delta | mu | kappa | delta agonist | delta antag. |
| 3 | [structure] | 8.8 | 6 | n.d. | 7.3 | 5 |
| 38 | [structure] | 8.7 | 6 | n.d. | n.d. | n.d. |
| 20 | [structure] | 8.6 | 6 | n.d. | 7 | 5 |

TABLE 7-continued

Results for the agonist receptor binding (pIC$_{50}$) and signal transport binding (pIC$_{50}$) testing.

| Comp. Nr. | Formula | Agonist receptor binding (pIC$_{50}$) | | | Signal transport binding (pIC$_{50}$) | |
|---|---|---|---|---|---|---|
| | | delta | mu | kappa | delta agonist | delta antag. |
| 102 | | 8.5 | 6 | n.d. | n.d. | n.d. |
| 25 | | 8.4 | 6 | n.d. | 6.9 | 5 |
| 2 | | 8.3 | 6 | n.d. | 6.8 | 5 |
| 41 | | 8.3 | 6 | n.d. | n.d. | n.d. |
| 98 | | 8.2 | 5.6 | 5.8 | 6.1 | 5 |

TABLE 7-continued

Results for the agonist receptor binding (pIC$_{50}$) and signal transport binding (pIC$_{50}$) testing.

| Comp. Nr. | Formula | Agonist receptor binding (pIC$_{50}$) | | | Signal transport binding (pIC$_{50}$) | |
|---|---|---|---|---|---|---|
| | | delta | mu | kappa | delta agonist | delta antag. |
| 19 | | 8.2 | 6 | n.d. | 6.5 | 5 |
| 24 | | 8.2 | 6 | n.d. | 6.9 | 5 |
| 1 | | 8.1 | 5 | 6.3 | n.d. | 5 |
| 31 | | 8.1 | 6 | n.d. | n.d. | n.d. |
| 12 | | 8.0 | 6 | n.d. | 7 | 5 | n.d.: not determined

The invention claimed is:

1. A compound selected from the group consisting of
1-ethoxycarbonyl-4-phenyl-4-[1-(phenylmethyl)-1-H-imidazol-2-yl]-piperidine;
1-propyloxycarbonyl-4-phenyl-4-[1-(phenylmethyl)-1-H-imidazol-2-yl]-piperidine;
1-ethoxycarbonyl-4-phenyl-4-[1-[(4-hydroxyphenyl)methyl]-1-H-imidazol-2-yl]-piperidine;
1-ethoxycarbonyl-4-phenyl-4-[1-(1-phenylethyl)-1-H-imidazol-2-yl]-piperidine;
1-isopropyloxycarbonyl-4-phenyl-4-[1-(phenylmethyl)-1-H-imidazol-2-yl]-piperidine;
1-ethoxycarbonyl-4-phenyl-4-[1-[[4-(methoxycarbonyl)phenyl]methyl]- -1-H imidazol-2-yl]-piperidine;
1-benzoyl-4-phenyl-4-[1-(phenylmethyl)-1H-imidazol-2-yl]-piperidine;
1-(methoxyacetyl)-4-phenyl-4-[1-(1-phenylethyl)-1-H-imidazol-2-yl]-piperidine;
4-[[2-(1-benzoyl-4-phenyl-4-piperidinyl)-1-H-imidazol-1-yl]methyl]-methylbenzoate;
4-[[2-[1-(2-benzoxazolyl)-4-phenyl-4-piperidinyl]-1-H-imidazol-1-yl]methyl]-methylbenzoate;
1-benzoyl-4-phenyl-4-[1-(1-phenylethyl)-1-H-imidazol-2-yl]-piperidine;
1-ethoxycarbonyl-4-phenyl-4-[1-[1-[4-(ethoxycarbonyl)phenyl]ethyl]-1-H imidazol-2-yl]-piperidine; and
N,4-diphenyl-4-[1-(phenylmethyl)-1-H-imidazol-2-yl]-1-Piperidinesulfonamide;
or a pharmaceutically acceptable acid or base addition salt thereof, a stereochemically isomeric form thereof, a tautomeric form thereof, or an N-oxide form thereof.

2. A pharmaceutical composition comprising a pharmaceutically acceptable carrier and, as active ingredient, a therapeutically effective amount of a compound according to claim 1, or a pharmaceutically acceptable acid or base addition salt thereof, a stereochemically isomeric form thereof, a tautomeric form thereof, or an N-oxide form thereof.

3. A method of treating a human suffering from a pain condition which comprises administering to the human in need of such a treatment a therapeutically effective amount of a compound according to claim 1, or a pharmaceutically acceptable acid or base addition salt thereof, a stereochemically isomeric form thereof, a tautomeric form thereof, or an N-oxide form thereof.

* * * * *

UNITED STATES PATENT AND TRADEMARK OFFICE
CERTIFICATE OF CORRECTION

PATENT NO. : 7,282,508 B2  Page 1 of 1
APPLICATION NO. : 10/491379
DATED : October 16, 2007
INVENTOR(S) : Frans Eduard Janssens et al.

It is certified that error appears in the above-identified patent and that said Letters Patent is hereby corrected as shown below:

Title Page,
Item (54) Title:
Delete "SUBSTITUTED 4-PHENYL-4-(1H-IMIDAZOL-2-YL)-PIPERIDINE DERIVATIVES AND THEIR USE AS SELECTIVE NON-PEPTIDE DELTA OPIOID AGONISTS" and insert -- SUBSTITUTED 4-PHENYL-4-{1H-IMIDAZOL-2-YL}-PIPERIDINE DERIVATIVES AND THEIR USE AS SELECTIVE NON-PEPTIDE DELTA OPIOID AGONISTS --.

Title Page,
Item (30) Foreign Application Priority Data:
After "01203926" insert -- .9 --.

Column 4,
Line 24, delete "$R^1$" and insert -- $R^6$ --.

Column 5,
Line 39, delete "-H-imidaxol-1-yl]" and insert -- -1H-imidaxol-1-yl] --.

Column 6,
Line 50, delete "S-[R,S*]." and insert -- S-[R*,S*]. --.

Column 51,
Line 38, delete "(13SA)" and insert -- (BSA) --.

Signed and Sealed this

Twenty-fourth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,282,508 B2  
APPLICATION NO. : 10/491379  
DATED : October 16, 2007  
INVENTOR(S) : Frans Eduard Janssens et al.

Page 1 of 1

It is certified that error appears in the above-identified patent and that said Letters Patent is hereby corrected as shown below:

Title Page,  
Item (54) and Column 1, lines 1-5, Title:  
Delete "SUBSTITUTED 4-PHENYL-4-(1H-IMIDAZOL-2-YL)-PIPERIDINE DERIVATIVES AND THEIR USE AS SELECTIVE NON-PEPTIDE DELTA OPIOID AGONISTS" and insert -- SUBSTITUTED 4-PHENYL-4-{1H-IMIDAZOL-2-YL}-PIPERIDINE DERIVATIVES AND THEIR USE AS SELECTIVE NON-PEPTIDE DELTA OPIOID AGONISTS --.

Title Page,  
Item (30) Foreign Application Priority Data:  
After "01203926" insert -- .9 --.

Column 4,  
Line 24, delete "$R^1$" and insert -- $R^6$ --.

Column 5,  
Line 39, delete "-H-imidaxol-1-yl]" and insert -- -1H-imidaxol-1-yl] --.

Column 6,  
Line 50, delete "S-[R,S*]." and insert -- S-[R*,S*]. --.

Column 51,  
Line 38, delete "(13SA)" and insert -- (BSA) --.

This certificate supersedes the Certificate of Correction issued February 24, 2009.

Signed and Sealed this

Seventeenth Day of March, 2009

JOHN DOLL  
*Acting Director of the United States Patent and Trademark Office*